US009632052B2

(12) United States Patent
Mieth et al.

(10) Patent No.: US 9,632,052 B2
(45) Date of Patent: Apr. 25, 2017

(54) MODULAR MEASURING DEVICE WITH DISTRIBUTED DATA AND ALGORITHMS

(75) Inventors: Tobias Mieth, Dresden (DE); Sven-Matthias Scheibe, Dresden (DE)

(73) Assignee: Endress+Hauser Conducta GmbH+Co. KG, Gerlingen (DE)

(*) Notice: Subject to any disclaimer, the term of this patent is extended or adjusted under 35 U.S.C. 154(b) by 613 days.

(21) Appl. No.: 13/126,634

(22) PCT Filed: Oct. 27, 2009

(86) PCT No.: PCT/EP2009/064124
§ 371 (c)(1),
(2), (4) Date: Apr. 28, 2011

(87) PCT Pub. No.: WO2010/049408
PCT Pub. Date: May 6, 2010

(65) Prior Publication Data
US 2011/0204876 A1    Aug. 25, 2011

(30) Foreign Application Priority Data

Oct. 30, 2008  (DE) .................. 10 2008 043 336

(51) Int. Cl.
*G01R 19/22*  (2006.01)
*G01N 27/28*  (2006.01)

(52) U.S. Cl.
CPC .................. *G01N 27/286* (2013.01)

(58) Field of Classification Search
CPC .................. G01N 27/4165; G01N 27/28
(Continued)

(56) References Cited

U.S. PATENT DOCUMENTS 7,248,182 B2 * 7/2007 Dudda et al. ............ 340/870.07
2002/0102884 A1 * 8/2002 Pechstein et al. ............ 439/660
(Continued)

FOREIGN PATENT DOCUMENTS

DE   102 18 606 A1   11/2003
DE   2005 044 973 A1   3/2007
(Continued)

OTHER PUBLICATIONS

Pechstein, DE10218606 machine translation, p. 1-13.*
(Continued)

*Primary Examiner* — Thomas Valone
(74) *Attorney, Agent, or Firm* — Christopher R. Powers; PatServe

(57) ABSTRACT

A sensor module includes a sensor element with a transducer for emitting an electric analog primary signal, which depends on a measured value; and a circuit assembly for conditioning the primary signal and for unidirectional data communication of a digital signal, which depends on the primary signal, to a superordinated unit. The circuit assembly has the following components: a signal input for receiving the primary signal, which depends on the measured value; a secondary side, inductively coupling, plug connector element for connection to a primary side, inductively coupling, plug connector element of the superordinated unit for receiving an energy signal and for transferring a measurement signal; an energy supply circuit, which rectifies the energy signal and provides at least one direct voltage for supplying the sensor module components; an analog signal conditioning circuit for conditioning the primary signal to a secondary signal; an analog-digital converter for converting the secondary signal to a digital measurement signal; a modulator for modulating the received energy signal for transferring the measurement signal to a superordinated unit (Continued)

by means of load modulation; and a microcontroller for controlling the components of the circuit assembly.

12 Claims, 1 Drawing Sheet

(58) Field of Classification Search
USPC .......................................................... 324/120
See application file for complete search history.

(56) References Cited

U.S. PATENT DOCUMENTS

2004/0075578 A1    4/2004  Dudda
2010/0216343 A1*  8/2010  Buschnakowski
                                    et al. ........................ 439/620.01

FOREIGN PATENT DOCUMENTS

| | | |
|---|---|---|
| DE | 10 2006 020 341 A1 | 10/2007 |
| DE | 102008055084 * 12/2008 | .................. 204/412 |
| DE | 10 2007 048 812 A1 | 4/2009 |
| DE | 10 2007 053 223 A1 | 5/2009 |
| EP | 1 206 012 A2 | 5/2002 |
| WO | WO 2005/031339 A1 | 4/2005 |

OTHER PUBLICATIONS

Babel, DE102006020341, machine translation, p. 1-19.*
Nelson, Todd, The Practical Limits of RS-485 (EIA-485), National Semiconductor, AN-979, Mar. 1995, p. 1-6.*

* cited by examiner

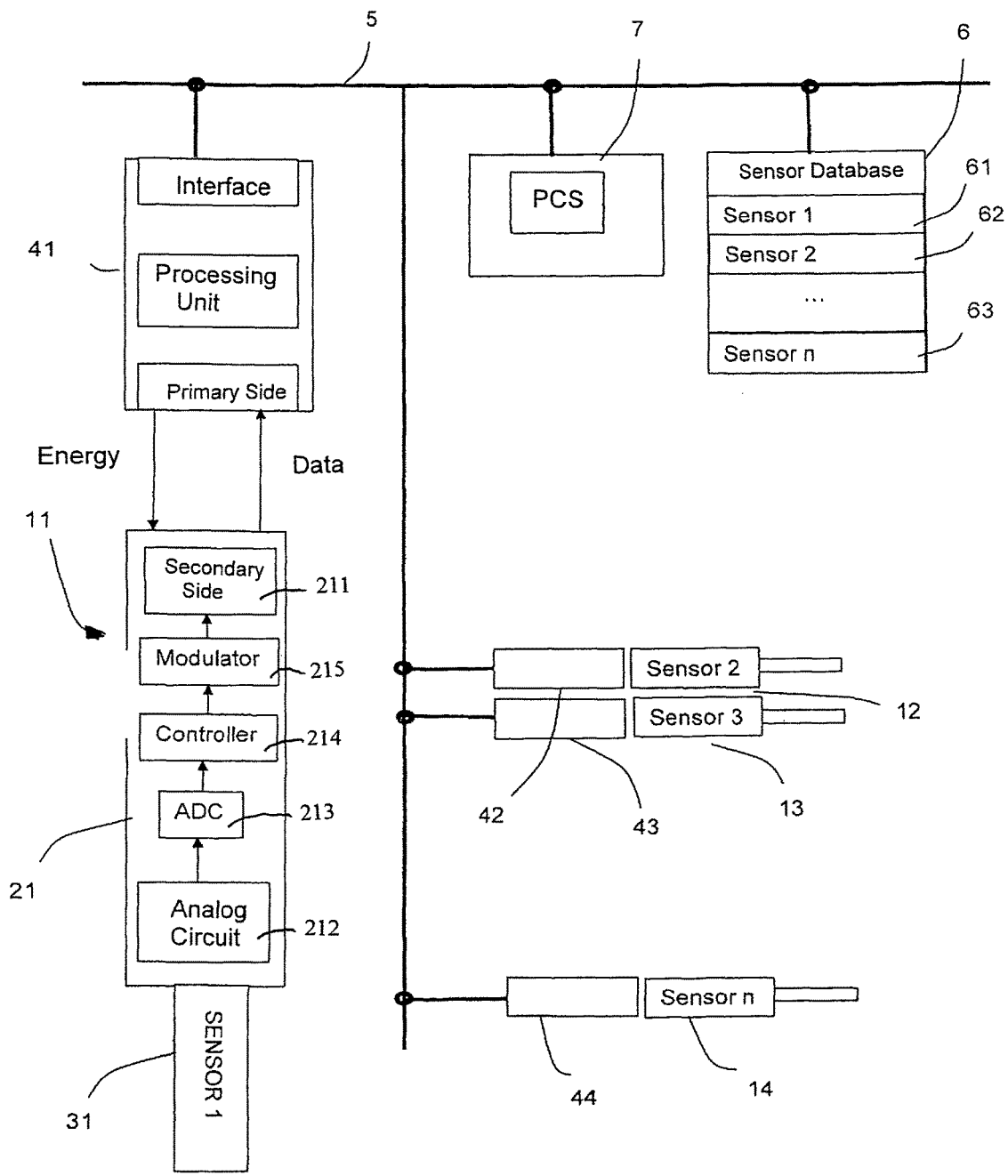

MODULAR MEASURING DEVICE WITH DISTRIBUTED DATA AND ALGORITHMS

TECHNICAL FIELD

The present invention relates to a sensor module.

BACKGROUND DISCUSSION

Modular measuring devices in the sense of the present invention are measuring devices with a sensor module and at least one superordinated module, for example, a measurement transmitter module, wherein the sensor module is coupled with the superordinated module via an interface. An example of a modular measuring device is, for example, a pH measuring device, in which the sensor module includes a pH electrode, especially in the form a single-rod measuring chain, wherein the sensor module is connected to a measurement transmitter module, which conditions a signal of the sensor module and transmits a signal corresponding to the measured value to a superordinated unit, for example, a control system.

The Endress+Hauser manufactures and sells modular pH measuring devices, in which the sensor module is connected via an interface, in the form an inductively coupling, pluggable, connector coupling, to the superordinated module, wherein the measurement transmitter module is associated with a primary side, plug connector element and the sensor module with a secondary side, plug connector element.

The fundamental principle of this interface is described in European Patent 1 206 012 B1. In accordance therewith, the energy supply of the sensor module and the data exchange between the sensor module and the measurement transmitter module occur via the inductive, pluggable, connector coupling. An inductively coupling, pluggable, connector coupling implements the supply of a consumer, e.g. a sensor module, by means of an energy signal, for example, an AC signal. The transmission of data, thus measurement data, or configuration and parameter data, can occur through modulation of the energy signal, for example, wherein the transmission of data by the energy receiving (secondary side) plug connector element from the energy dispensing (primary side) plug connector element can occur through load modulation of the energy signal. For the separating of data and energy, corresponding demodulators are usually provided. Details for this are disclosed in Patent DE 197 19 730 C1, for example. Inductively coupling sensor modules according to the state of the art have the following circuit parts: Voltage supply including a secondary coil, modulator, demodulator, microcontroller, external memory elements (e.g. EEPROM), analog amplifier, and analog-digital converter.

All of the circuit parts named above are used to ascertain, to handle, and on request, transfer the measured value to a superordinated module via the inductively coupling, pluggable, connector coupling. Furthermore, measuring device adjustment values, calibration values, operating hours, etc. are stored in the microcontroller or in the external memory element. In the course of its life, a sensor module stores a relatively large amount of data. This data can be accessed, depending on need, by the superordinated module, whether it is a measurement transmitter or an interface to a process control system.

However, it is to be taken into consideration that for the communication of the named data between measurement transmitter and sensor module, a communication protocol is required. This must be carried out by the sensor completely in one protocol stack. This requires memory capacity and corresponding hardware in the microcontroller. Furthermore, a demodulator, which demodulates the queries of the measurement transmitter and makes them accessible to the microcontroller, is necessary.

For managing and performing the named tasks of the sensor module, a microcontroller is necessary, which implements the recording of the measured value, communication and data storage. This requires a sufficient number of I/O pins, a high powered CPU and a large amount of program memory (flash) and working memory RAM.

The external or internal memory elements of such a sensor module are sized for the longest expected period of use of the sensor module. If the sensor modules are applied at measuring points characterized by a high loading of the sensor module, because of aggressive media, for example, then the life expectancy shrinks significantly and the sensor module has more memory available than it can ever use. Thus, then, the available memory capacity is disposed of along with the sensor module.

Of course, the microcontroller is also disposed of along with the sensor module.

The purchase and disposal of short lived sensor modules, for example, pH sensors with pH glass electrode, lead to unnecessarily high costs.

SUMMARY OF THE INVENTION

Corrections of errors or adaptations in the software of a sensor module are either not possible or require complex reprogramming of each individual sensor module.

Therefore, it is an object of the present invention to provide a modular measuring device which overcomes the described disadvantages of the state of the art.

According to the invention, the object is achieved by the sensor module defined in claim 1, by the modular measuring device defined in independent patent claim 6 and the method for determining a measured variable as defined in claim 11.

The sensor module of the invention comprises:

A sensor element with a transducer for emitting an analog primary signal, which depends on a measured value; and a circuit assembly for conditioning the primary signal and for unidirectional data communication of a digital signal, which depends on the primary signal, to a superordinated unit connected to the sensor module, wherein the circuit assembly has the following components:

a signal input for receiving the primary signal, which depends on a measured value;

a secondary side, inductively coupling, plug connector element having a secondary coil for connection to a primary side, inductively coupling, plug connector element of the superordinated unit for receiving an inductively transmitted, energy signal from the primary side, inductively coupling, plug connector element and for transferring a measurement signal to the primary side, inductively coupling, plug connector element;

an energy supply circuit, which rectifies the received energy signal and provides at least one direct voltage for supplying the circuit assembly, and, in given cases, the sensor element;

an analog signal conditioning circuit for conditioning the received primary signal to an analog, secondary signal;

an analog-digital converter for converting the analog, secondary signal to a digital measurement signal;

a modulator for modulating the received energy signal for transferring the digital measurement signal to a superordinated unit by means of load modulation; and a microcontroller for controlling the components of the circuit assembly.

With the circuit parts mentioned above, the sensor module is able to ascertain a measured value and transmit derived measurement data to a superordinated measurement transmitter.

In such case, especially, a demodulator and external memory elements, i.e. memory elements outside of the microcontroller, are omitted. Thus, the sensor module is not able to receive information from the measurement transmitter; it can only transmit data.

All important data concerning the sensor module are centrally or decentrally stored in a superordinated unit, or in a network, to which the sensor module is connected. The sensor module includes a unique identification number IDN, in order to associate the associated data uniquely.

For example, each measurement data transmission in the form of a communication telegram from the sensor module contains the IDN, the digital measurement signal, and in given cases, a test sum or status information.

The status information serves, for example, for error detection or for error signaling.

The modular measuring device of the invention includes a sensor module of the invention and a superordinated unit, which is connected to the sensor module, wherein the superordinated unit is provided to receive a digital measurement signal from the sensor module and, taking into consideration calibration data associated with the sensor module, to calculate a measured value based on the measurement signal, wherein the calibration data are exclusively provided from outside the sensor module.

In a further development of the measuring device, the superordinated unit comprises a measurement transmitter, which communicates with a database via a bus system, or a network, in order to access calibration data associated with the sensor module.

In a further development of the measuring device, the superordinated unit includes a control system, which communicates with a database via a bus system, or a network, in order to access calibration data associated with the sensor module.

The sensor module can transmit the digital measurement signal, for example, with such a data rate as the measured value recording permits. Thus, a predetermined time regime of the superordinated unit is not required.

In a further development of the invention, an encrypted transmission of the communication telegram is provided.

The sensor module or the measuring device of the invention has, as a result, the following advantages, for example:

Short lived sensor modules, for example, sensor modules with pH glass electrodes, can be manufactured more inexpensively because fewer electronic components are used.

The microcontroller applied can be of very much smaller size, because it must manage only a very simple communication protocol.

As regards data storage in the sensor module, there is little, or no, need.

All sensor data are available outside the sensor module in the superordinated unit or in a network connected to the superordinated unit. Therewith, data of the sensor modules used at the moment in a process installation are available at any time. Also the sensor modules can be calibrated in the laboratory, wherein the calibration data associated with a sensor module is provided in the network based on the calibrating.

So long as a sensor module sends data, these data can, according to a further development of the invention, be secured in a database.

After disposal of worn out or defective sensors, all data can be archived and are thus available for subsequent analyses.

Virtually unlimited memory capacity is available in the network to long lived sensors. In general, as much memory as actually required is available for each sensor.

Development of sensors is able to occur faster, because fewer tests, especially communication tests, need to be performed.

Calculating algorithms can be adapted or optimized during the lifetime of the sensor. Thus, the data of all sensors being used at the time of an update, as well also the data of older sensors, immediately enjoy the benefit of optimized algorithms.

In a further development of the invention, parts of the analog circuit and/or of the microcontroller can be combined in FPGAs or ASICs or others. This further reduces costs and requirement for space.

The method of the invention for determining a measured variable can proceed as follows:

i. The sensor module is connected to a primary side, inductively coupling, pluggable, connector coupling and the microcontroller is initialized.

ii. Immediately after initializing the microcontroller, recording the measured value begins.

iii. As soon as the first measurement data are ascertained, these are sent by means of the modulator, via the primary side, inductively coupling, plug connector element, to a superordinated unit by means of a simple communication telegram, which contains a digital measurement signal, the IDN and, in given cases, a test sum and/or status information.

iv. The superordinated unit identifies the sensor module based on the IDN and receives the digital measurement signal of the sensor.

Based on measuring device adjustment and calibration values stored for this sensor module, the actual measured value can now be calculated with the help of the calculating algorithms and, in given cases, output.

BRIEF DESCRIPTION OF THE DRAWINGS

The invention will now be explained based on an example of an embodiment illustrated in the drawing, the sole FIGURE of which shows as follows:

FIG. 1 is a schematic representation of a modular measuring device in a network.

DETAILED DISCUSSION IN CONJUNCTION WITH THE DRAWING

The network 5 in FIG. 1 can comprise, for example, a fieldbus or an Ethernet network. Connected to the network is a sensor module 11, which includes a circuit assembly 21 and a sensor element 31. The sensor element 31 comprises especially a pH glass electrode in the form a single-rod measuring chain.

The circuit assembly 21 includes a secondary side, inductively coupling, plug connector element 211 having a secondary coil for receiving an AC energy signal and an energy supply unit for converting the AC energy signal to at least one direct voltage for feeding the components of the sensor module 11.

The circuit assembly 21 includes furthermore an analog circuit 212 for conditioning the pH dependent potential of the single-rod measuring chain, which is fed as a primary signal to the analog circuit 212. Furthermore, the circuit assembly 21 includes an analog-digital converter 213, which digitizes the conditioned analog, secondary signal and then sends it to a microcontroller 214. The digitized measurement signal is transmitted, together with an identification number IDN of the sensor module as well as a test sum and status information, by a modulator 215, by means of load modulation of the AC energy signal, to a primary side, inductively coupling, plug connector element 41 in the form of a communication telegram.

The primary side, inductively coupling, plug connector element 41 feeds the AC energy signal to the sensor module 11 and is connected to the network, wherein the secondary side plug connector element 41 has a processing unit with a demodulator, in order to convert and output the received communication telegram in the protocol of the network.

For ascertaining the actual measured value, based on the IDN of the sensor module, the required calibration values for the zero point and slope of the single-rod measuring chain 11 are fetched from the associated calibration data set 61 of a sensor database 6 of the process control system 7 via the network 5. The process control system ascertains the current value of the measured variable based on the calibration data set and digital measurement signal. The historical data of the continually ascertained, measured values can be stored in a suitable location in the network, for example, in the sensor database 6.

Besides the sensor module 11 described in detail, other sensor modules 12, 13, 14 can be connected to the network via inductively coupling, primary side, plug connector elements 42, 43, 44.

The calibration data of all sensor modules which are operating in the network are ready in the sensor database. Of course, calibration data of sensors whose start up is imminent can also be provided in the database.

The invention claimed is:

1. A method for determining a measured variable, with a measuring device, comprising the steps of:
    connecting a sensor module to a primary side, inductively coupling, plug connector element and initializing the sensor module;
    beginning measured value recording directly after initializing the sensor module, wherein said measured values are analog values;
    converting said analog values into digital values;
    sending said digital values via a network, the network including a fieldbus or an ethernet network, to a superordinated unit by means of a communication telegram, wherein the communication telegram contains said digital values and a unique identification number, wherein said sensor module can only send said digital values and is not able to receive information from said superordinated unit;
    identifying said sensor module by the superordinated unit based on said unique identification number; and
    calculating the actual measured variable in said superordinated unit from said digital values with the help of calculating algorithms, based on required measuring device adjustment and calibration values associated with said sensor module and stored for said sensor module in said superordinated unit or said network, wherein the calibration values are exclusively provided from outside the sensor module.

2. The method as claimed in claim 1, wherein:
the communication telegram further contains a test sum and/or status information, for error detection.

3. The method as claimed in claim 1, wherein:
said calibration values are stored in a sensor database in said superordinated unit or said network.

4. The method as claimed in claim 1, wherein:
historical data of said measured variable are stored in said network.

5. The method as claimed in claim 4, wherein:
said historical data are stored in a sensor database in said superordinated unit or said network.

6. The method as claimed in claim 1, wherein:
said communication telegram is converted and output in a protocol of said network.

7. The method as claimed in claim 1, wherein:
said digital values are converted into said communication telegram by means of load modulation.

8. The method as claimed in claim 1, wherein:
said measuring device comprises a pH glass electrode in form of a single-rod measuring chain.

9. The method as claimed in claim 8, wherein:
said calibration values comprise a zero point and slope of said single-rod measuring chain.

10. The method as claimed in claim 1, wherein:
other measuring devices are connected to said network via inductively coupling, plug connector elements.

11. The method as claimed in claim 10, wherein:
calibration values of all measuring devices operating in said network are stored in a sensor database in said superordinated unit or said network.

12. The method as claimed in claim 10, wherein:
calibration values of measuring devices whose startup is imminent are stored in a sensor database in said superordinated unit or said network.

* * * * *